(12) United States Patent
Chan et al.

(10) Patent No.: US 11,957,804 B2
(45) Date of Patent: Apr. 16, 2024

(54) OPTICAL DISINFECTION SYSTEMS HAVING SIDE-EMITTING OPTICAL FIBER COUPLED TO HIGH-ENERGY UV-C LASER DIODE

(71) Applicant: The Boeing Company, Chicago, IL (US)

(72) Inventors: Eric Y. Chan, Mercer Island, WA (US); Dennis G. Koshinz, Bellevue, WA (US); Kim Quan Anh Nguyen, Seattle, WA (US); Lyndon G. Mazon, Lynnwood, WA (US)

(73) Assignee: The Boeing Company, Arlington, VA (US)

( * ) Notice: Subject to any disclaimer, the term of this patent is extended or adjusted under 35 U.S.C. 154(b) by 327 days.

(21) Appl. No.: 17/395,734

(22) Filed: Aug. 6, 2021

(65) Prior Publication Data

US 2022/0096677 A1 Mar. 31, 2022

Related U.S. Application Data

(60) Provisional application No. 63/084,462, filed on Sep. 28, 2020.

(51) Int. Cl.
*A61L 2/00* (2006.01)
*A61L 2/10* (2006.01)
(Continued)

(52) U.S. Cl.
CPC .............. *A61L 2/10* (2013.01); *G02B 6/0006* (2013.01); *G02B 6/001* (2013.01); *B64F 5/30* (2017.01)

(58) Field of Classification Search
CPC ......... G02B 6/001; G02B 6/0006; A61L 2/10; A61L 2/0047; A61L 2209/12;
(Continued)

(56) References Cited

U.S. PATENT DOCUMENTS

| 4,130,345 A | * | 12/1978 | Doellner | G02B 6/2817 385/47 |
| 4,173,390 A | * | 11/1979 | Kach | G02B 6/2817 385/47 |

(Continued)

OTHER PUBLICATIONS

Zhang et al., "A 271.8 nm deep-ultraviolet laser diode for room temperature operation", Applied Physics Express, 12, Nov. 7, 2019.

(Continued)

*Primary Examiner* — Sean M Luck
(74) *Attorney, Agent, or Firm* — Ostrager Chong Flaherty & Broitman P.C.

(57) ABSTRACT

High-energy optical disinfection systems inside a commercial airplane using highly efficient, flexible, and durable side-emitting optical fibers optically coupled to high-energy UV-C laser diodes to destroy submicroscopic infectious agents and inactivate microorganisms inside the airplane. With the high-energy UV-C laser diodes optically coupled to the side-emitting optical fibers, which can be easily routed to different areas inside the airplane, the high-energy UV-C laser light emitted from the side of the optical fiber will disinfect the airplane along a wide or long swath continuously without interruption.

20 Claims, 15 Drawing Sheets

(51) Int. Cl.
*F21V 8/00* (2006.01)
*B64F 5/30* (2017.01)

(58) Field of Classification Search
CPC .... A61L 2209/15; A61L 9/20; A61L 2202/11; A61L 2202/16; B64F 5/30
See application file for complete search history.

(56) References Cited

U.S. PATENT DOCUMENTS

| | | | | |
|---|---|---|---|---|
| 4,802,727 | A * | 2/1989 | Stanley | G01J 3/26 250/227.24 |
| 4,897,711 | A * | 1/1990 | Blonder | G02B 6/4214 257/729 |
| 5,071,213 | A * | 12/1991 | Chan | G02B 6/4214 385/38 |
| 5,181,263 | A * | 1/1993 | Derfiny | G02B 6/4202 385/24 |
| 5,351,331 | A * | 9/1994 | Chun | G02B 6/4202 385/91 |
| 5,808,708 | A * | 9/1998 | Oyama | G02B 6/0018 362/621 |
| 5,883,988 | A * | 3/1999 | Yamamoto | G02B 6/42 257/E31.128 |
| 5,896,481 | A * | 4/1999 | Beranek | G02B 6/4248 385/91 |
| 6,104,857 | A * | 8/2000 | Ishiharada | G02B 6/02033 385/141 |
| 6,438,297 | B1 * | 8/2002 | McKenzie | G02B 6/423 385/38 |
| 6,614,963 | B2 * | 9/2003 | Melchior | G02B 6/4257 385/47 |
| 6,786,654 | B2 * | 9/2004 | Kilian | G02B 6/4248 385/94 |
| 6,954,592 | B2 * | 10/2005 | Tan | H04B 10/43 398/138 |
| 7,188,988 | B2 * | 3/2007 | Koganezawa | G02F 1/133603 362/616 |
| 8,085,359 | B2 * | 12/2011 | Olson | G02B 6/002 362/97.3 |
| 8,582,943 | B2 | 11/2013 | Alkemper et al. | |
| 9,268,082 | B2 * | 2/2016 | Van Dijk | G02B 6/0078 |
| 9,329,318 | B2 | 5/2016 | Russert | |
| 9,581,772 | B2 * | 2/2017 | Lan | G02B 6/4214 |
| 9,778,419 | B1 * | 10/2017 | Chan | G02B 6/262 |
| 10,261,229 | B2 | 4/2019 | Woelfing et al. | |
| 10,261,230 | B2 | 4/2019 | Gaydoul et al. | |
| 10,309,614 | B1 * | 6/2019 | Jones | F21V 7/041 |
| 10,551,542 | B1 * | 2/2020 | Tan | H01L 33/58 |
| 10,569,699 | B2 | 2/2020 | Schabacker et al. | |
| 2006/0262564 | A1 * | 11/2006 | Baba | G02B 6/0021 362/616 |
| 2007/0189677 | A1 * | 8/2007 | Murry | G02B 6/4279 385/92 |
| 2008/0008620 | A1 * | 1/2008 | Alexiadis | F21S 4/26 422/186.3 |
| 2008/0151553 | A1 * | 6/2008 | Okamoto | H04N 1/02815 362/328 |
| 2009/0052207 | A1 * | 2/2009 | Chen | G02B 6/001 362/616 |
| 2009/0067799 | A1 * | 3/2009 | Nakane | G02B 6/4214 385/131 |
| 2009/0287197 | A1 * | 11/2009 | Hanley | A61B 18/24 385/38 |
| 2011/0075441 | A1 * | 3/2011 | Swessel | F21S 8/033 362/509 |
| 2011/0102707 | A1 * | 5/2011 | Yoo | G02B 6/0085 349/62 |
| 2011/0103757 | A1 * | 5/2011 | Alkemper | G02B 6/001 385/124 |
| 2014/0078772 | A1 * | 3/2014 | Gaydoul | F21S 43/245 362/555 |
| 2014/0286363 | A1 * | 9/2014 | Kasai | H01S 5/02251 228/101 |
| 2016/0085027 | A1 * | 3/2016 | Chan | G02B 6/266 385/24 |
| 2016/0184467 | A1 * | 6/2016 | Cheng | C02F 1/325 250/492.1 |
| 2017/0081874 | A1 * | 3/2017 | Daniels | E05B 1/0015 |
| 2017/0166118 | A1 * | 6/2017 | Saul | B60Q 3/80 |
| 2019/0381203 | A1 * | 12/2019 | Zaborsky | A61L 2/10 |
| 2020/0183070 | A1 * | 6/2020 | Tan | G02B 6/036 |

OTHER PUBLICATIONS

Lawal et al., "UV-C LED Devices and Systems: Current and Future State", IUVA News, vol. 20, No. 1, Mar. 2018.
Schott HelioLine Datasheet, undated, but the disclosed product (High-quality Aviation approved side-emitting glass fiber cable) is prior art and the unknown month and year of date of first publication is not material.

* cited by examiner

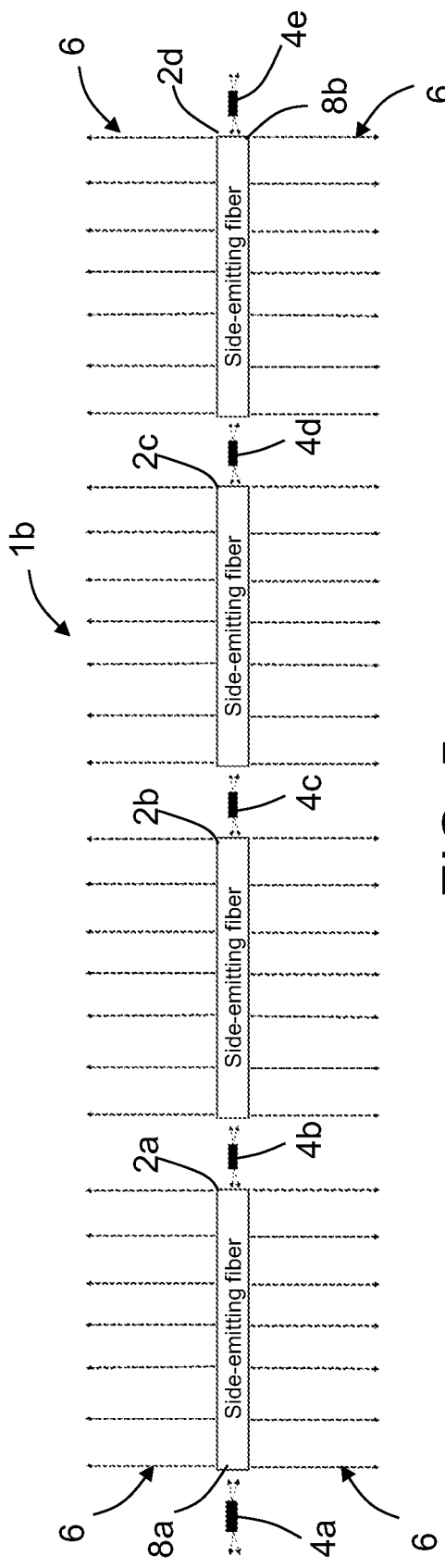
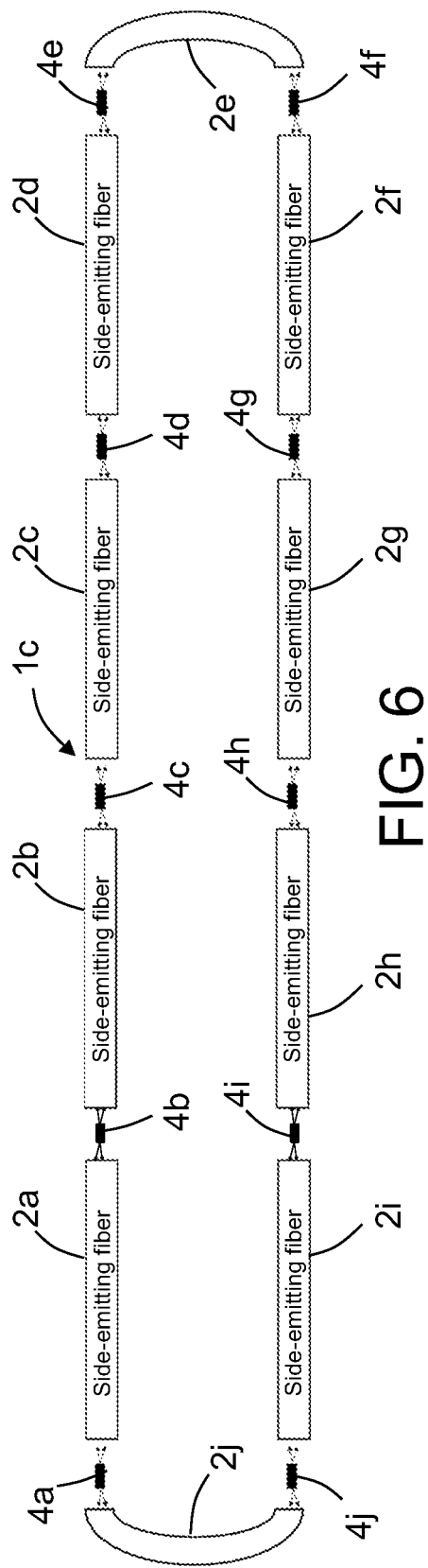
FIG. 5
FIG. 6

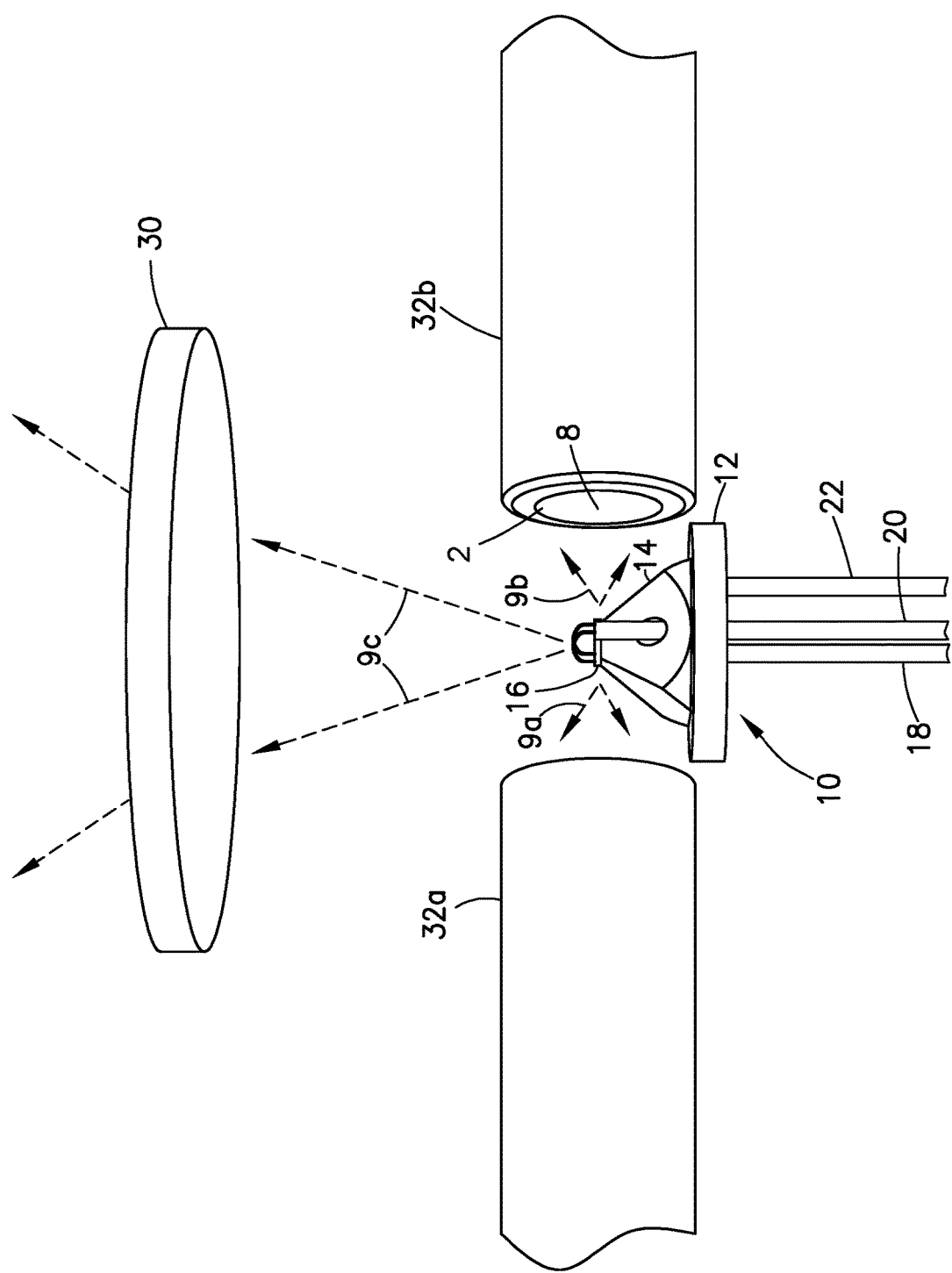

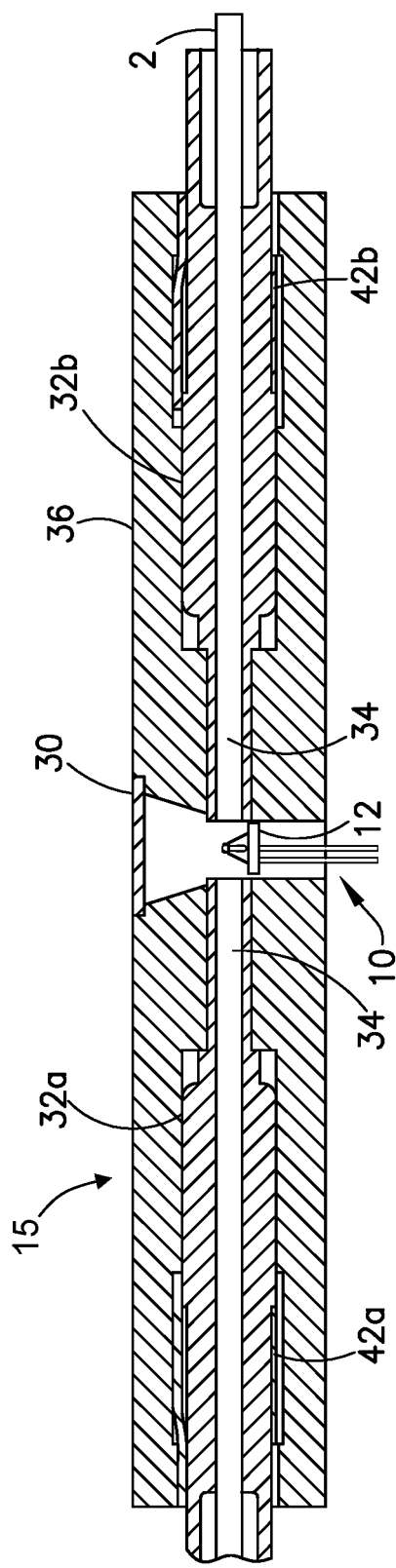
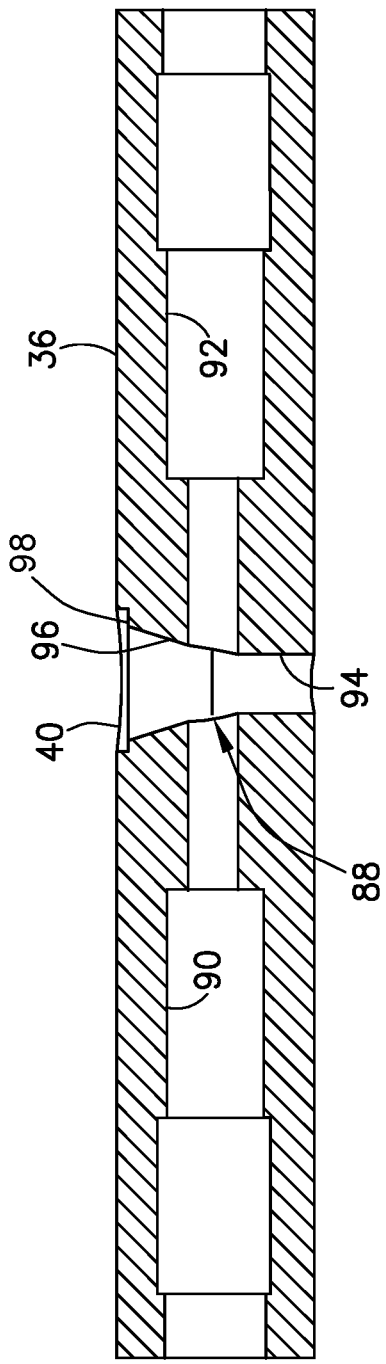
FIG. 9A
FIG. 9B

OPTICAL DISINFECTION SYSTEMS HAVING SIDE-EMITTING OPTICAL FIBER COUPLED TO HIGH-ENERGY UV-C LASER DIODE

RELATED PATENT APPLICATION

This application claims the benefit, under Title 35, United States Code, Section 119(e), of U.S. Provisional Application No. 63/084,462 filed on Sep. 28, 2020.

BACKGROUND

This disclosure generally relates to design and fabrication of systems for destroying or inactivating pathogenic agents (such as bacteria, protozoans, and viruses). In particular, this disclosure relates to ultraviolet light-emitting assemblies for use in disinfection systems.

Ultraviolet germicidal irradiation (UVGI) is a disinfection method that uses ultraviolet C (UV-C) light to kill submicroscopic infectious agents and inactivate microorganisms. UV-C light has wavelengths in the range of 100-280 nm. According to the Centers for Disease Control and Prevention, the maximum bactericidal effect occurs at 240-280 nm. The application of UV-C light has proven to be effective in destroying submicroscopic infectious agents and inactivating microorganisms on surfaces.

Existing solutions use individual UV light-emitting diodes (LEDs) or mercury lamps as a source to perform disinfection. However, implementing a large number of UV LEDs and mercury lamps inside a commercial airplane is not very efficient for disinfection because UV LEDs are not emitting UV-C photons efficiently compared to a laser light source, whereas mercury lamps are not preferred light sources because the lamps contain mercury, which is an environmental hazard. Besides, using individual LEDs and mercury lamps cannot cover a wide and lengthy area in a commercial airplane, and installing an LED array and mercury lamps in tight space locations inside a commercial airplane is very expensive and may be impractical. Examples of such areas are the flight deck, lavatories, flight attendant stations, passenger cabin, cargo compartments, and electronics bays.

The cost of parking an airplane on the ground to undergo disinfection is large. Systems capable of assuring that the airplane is free of pathogens with very low cost of operation would be beneficial. Accordingly, an effective optical disinfection system that can quickly disinfect difficult-to-access areas inside an airplane without human intervention is desired.

SUMMARY

The subject matter disclosed in some detail below is directed to the implementation of high-energy optical disinfection systems inside a commercial airplane using highly efficient, flexible, and durable side-emitting optical fibers optically coupled to high-energy UV-C laser diodes to destroy submicroscopic infectious agents and inactivate microorganisms inside the airplane. With the high-energy UV-C laser diodes optically coupled to the side-emitting optical fibers, which can be easily routed to different areas inside the airplane, the high-energy UV-C laser light emitted from the side of the optical fiber will disinfect the airplane along a wide or long swath continuously without interruption. The proposed systems will assure that the airplane is free of pathogens with a very low cost of operation.

The embodiments of optical disinfection systems disclosed herein use high-efficiency side-emitting optical fiber to route UV-C laser light to different areas inside the airplane, such as the flight deck, lavatories, flight attendant stations, passenger cabin, cargo compartments, and electronics bays. A high-energy UV-C laser light source is selected which can be operated in a low-duty-cycle pulse mode, burst mode, or continuous mode to disinfect airborne or surface-borne pathogens (e.g., virus) inside the airplane.

As used herein, the term "optical fiber" has either of two meanings depending on the context in which the term is used. In some instances (for example, in the claims), the term is used without the preceding article "an" to refer to optical fiber in general as a type of structural element; in other instances, the term is used with the preceding article "an" to specifically refer to a single optical fiber. For avoidance of doubt, the term "optical fiber" without "an" (and without "a single"), as appears in the claims, should be construed to encompass at least a single optical fiber (e.g., formed as a loop with ends confronting opposite edges of a laser diode) or first and second optical fibers (e.g., having respective ends confronting opposite edges of a laser diode).

The benefits of using side-emitting optical fiber are manifold. Side-emitting optical fiber of relatively large diameter is very flexible and durable, and the cost of installing optical fiber in an airplane is relatively low. Side-emitting optical fiber can deliver UV-C light to a large area inside the airplane as compared to approaches using individual UV LEDs and mercury lamp sources. Side-emitting optical fiber can deliver UV-C light efficiently to difficult-to-access tight spaces or covered areas inside the airplane, thereby enhancing the efficiency of the disinfection process onboard the airplane without human intervention. The side-emitting optical fibers are optically coupled to UV-C laser diodes for continuous illumination, the individual assemblies being routed through selected areas inside the airplane to provide long-lasting disinfection. In accordance with one proposed implementation designed to kill virus, the laser diode is operated in pulse mode for effective disinfection, because fast laser pulses kill the virus faster in a much shorter time than the virus replication time.

Although various embodiments of optical disinfection systems having side-emitting optical fiber optically coupled to a UV-C laser diode will be described in some detail below, one or more of those embodiments may be characterized by one or more of the following aspects.

One aspect of the subject matter disclosed in detail below is an optical disinfection system comprising: a first laser diode configured to emit UV-C laser light; and a first side-emitting optical fiber having a first end face disposed to receive UV-C laser light emitted by the first laser diode. In accordance with some embodiments, the first side-emitting optical fiber forms a loop and a second end face of the first side-emitting optical fiber is disposed to receive UV-C laser light emitted by the first laser diode. In accordance with other embodiments, the optical disinfection system further comprises a second laser diode configured to emit UV-C laser light, wherein a second end face of the first side-emitting optical fiber is disposed to receive UV-C laser light emitted by the second laser diode.

Another aspect of the subject matter disclosed in detail below is an optical disinfection system comprising: a multiplicity of side-emitting optical fibers arranged in sequence along a line with spacing between adjacent side-emitting optical fibers, each side-emitting optical fibers having a pair of end sections with respective end faces; a multiplicity of pairs of termini, each terminus surrounding an end section of one of the multiplicity of side-emitting optical fibers; a multiplicity of housings arranged in sequence along the line with spacing between adjacent housings, each housing supporting a respective pair of termini; and a multiplicity of laser diodes configured to emit UV-C laser light, each laser diode being housed in a respective housing, wherein each side-emitting optical fiber receives UV-C laser light at opposite end faces thereof from a respective pair of laser diodes.

A further aspect of the subject matter disclosed in detail below is a method for disinfecting using UV-C laser light, the method comprising: (a) affixing a side-emitting optical fiber to a structure; (b) emitting first UV-C laser light which enters one end face of the side-emitting optical fiber; (c) emitting second UV-C laser light which enters another end face of the side-emitting optical fiber; and (d) side-emitting at least some of the first and second UV-C laser light from the side-emitting optical fiber. In accordance with one embodiment, the first UV-C laser light is emitted from a first facet of an edge-emitting laser diode and the second UV-C laser light is emitted from a second facet of the edge-emitting laser diode. In accordance with another embodiment, the first UV-C laser light is emitted from a facet of a first edge-emitting laser diode and the second UV-C laser light is emitted from a facet of a second edge-emitting laser diode.

Other aspects of optical disinfection systems having side-emitting optical fiber optically coupled to a UV-C laser diode are disclosed and claimed below.

BRIEF DESCRIPTION OF THE DRAWINGS

The features, functions and advantages discussed in the preceding section can be achieved independently in various embodiments or may be combined in yet other embodiments. Various embodiments will be hereinafter described with reference to drawings for the purpose of illustrating the above-described and other aspects. None of the diagrams briefly described in this section are drawn to scale.

FIG. 5 is a diagram showing uniform light emission from four side-emitting optical fibers interleaved to receive UV-C laser light from five UV-C laser diodes.

FIG. 6 is a diagram showing a closed-loop arrangement of ten side-emitting optical fibers interleaved with ten edge-emitting UV-C laser diodes to illuminate a large and long rectangular area for virus disinfection in accordance with one proposed implementation.

FIG. 8 is a diagram representing a three-dimensional view of some components of an optical subassembly in accordance with one embodiment. The housing of the optical subassembly has been omitted to reveal a laser package (of the type depicted in FIG. 2) situated between respective end faces of respective end sections of side-emitting optical fiber and beneath a transparent window. The dashed arrows represent UV-C laser light emitted by the laser diode.

FIG. 9A is a diagram representing a sectional view of an optical subassembly that includes the laser package depicted in FIG. 7. Only the laser package and the optical fibers are not sectioned.

FIG. 9B is a diagram representing a sectional view of an optical subassembly housing which is included in the optical subassembly depicted in FIG. 9A.

Reference will hereinafter be made to the drawings in which similar elements in different drawings bear the same reference numerals.

DETAILED DESCRIPTION

Figure 1:
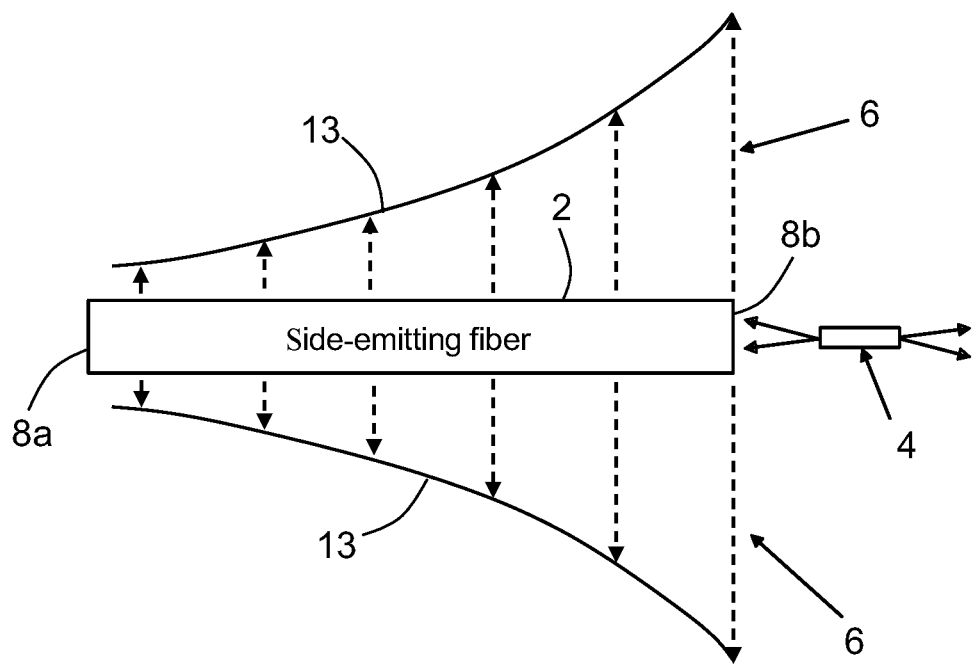
FIG. 1 is a diagram showing a UV-C light intensity profile along a side-emitting optical fiber with one end face optically coupled to a UV-C edge-emitting laser diode.

Illustrative embodiments of optical disinfection systems having side-emitting optical fiber optically coupled to a UV-C laser diode are described in some detail below. However, not all features of an actual implementation are described in this specification. A person skilled in the art will appreciate that in the development of any such embodiment, numerous implementation-specific decisions must be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

There are three bands of UV light source available for disinfection: the UV-A, UV-B, and UV-C bands. But only the UV-C band in the wavelength range of 200 nm to 280 nm is effective for disinfection applications. Commercially available UV LEDs are mainly in the UV-A and UV-B bands. Also, an LED is not efficient in generating sufficiently high power to couple to an optical fiber for a long-distance disinfection application.

Using a laser to generate UV-C light has some challenges in device fabrication. UV-C light photons are higher energy than the UV-A and UV-B photons. Therefore, the light generated in the active layer of the laser diode is absorbed by the light-guiding layer above and below the active layer of the UV-C laser diode before it can be output to the edges of the laser diode.

To overcome the foregoing problem, the light-guiding layer of the UV-C laser diode must have a much higher band-gap than the active layer. The higher band-gap layers are difficult to fabricate because these layers have a much larger lattice constant (or size), which causes lattice mismatch with the laser substrate and the active layer. The lattice mismatch produces defects in the active layers which reduce the effective stimulated UV-C laser light emission in the laser structure.

For the purpose of illustration, UV-C optical disinfection systems configured for installation inside an airplane will now be described. The disclosed systems use side-emitting optical fibers and UV-C edge-emitting laser diodes. This combination of optical elements enables the cost-effective installation of a highly effective virus optical disinfection system which may be operated without human intervention. Although the proposed implementations disclosed herein are inside an airplane, UV-C optical disinfection systems having side-emitting optical fiber and UV-C edge-emitting laser diodes are also applicable to use in hospitals, ships, churches, grocery stores, shopping malls, automobiles, sports stadiums, movie theaters, and any other structure that would benefit from highly efficient virus disinfection.

Using side-emitting optical fiber to transmit robust UV-C laser light along a long distance inside an airplane requires pumping the optical fiber at both ends. This phenomenon is attributable to the fact that the intensity of light entering at one end face of the side-emitting optical fiber is reduced as the light propagates along the length of the side-emitting optical fiber. By injecting UV-C light at both ends of the side-emitting optical fiber, the uniformity of light emitting from the side of the optical fiber is assured. The principle and design of two-end light injection to achieve uniform side emission of light along the side-emitting optical fiber is employed in the proposed implementations depicted in FIGS. 1-6.

FIG. 1 is a diagram showing a UV-C light intensity profile 13 along a side-emitting optical fiber 2 with one end face 8b optically coupled to a UV-C edge-emitting laser diode 4. (For the sake of illustration, no UV-C laser light enters the side-emitting optical fiber 2 via end face 8a.) FIG. 1 includes solid arrows representing UV-C laser light exiting both of the front and rear facets of the UV-C edge-emitting laser diode 4. The UV-C edge-emitting laser diode 4 may be configured to provide equal coherent light emission at both front and back facets. FIG. 1 further includes dashed arrows representing UV-C laser light 6 being side-emitted in opposite directions in the same plane. However, it should be appreciated that the "side" of the side-emitting optical fiber 2 is a circular cylindrical circumference and that the internal structure of the side-emitting optical fiber 2 is configured to emit light radially outward over a full 360 degrees, so that UV-C laser light is emitted in all directions perpendicular to the axis of the optical fiber. Because of the side emission of the optical fiber, the intensity of the UV-C light emitted from the side of the optical fiber decreases with distance along the optical fiber, as shown by the intensity profile 13.

Figure 2:
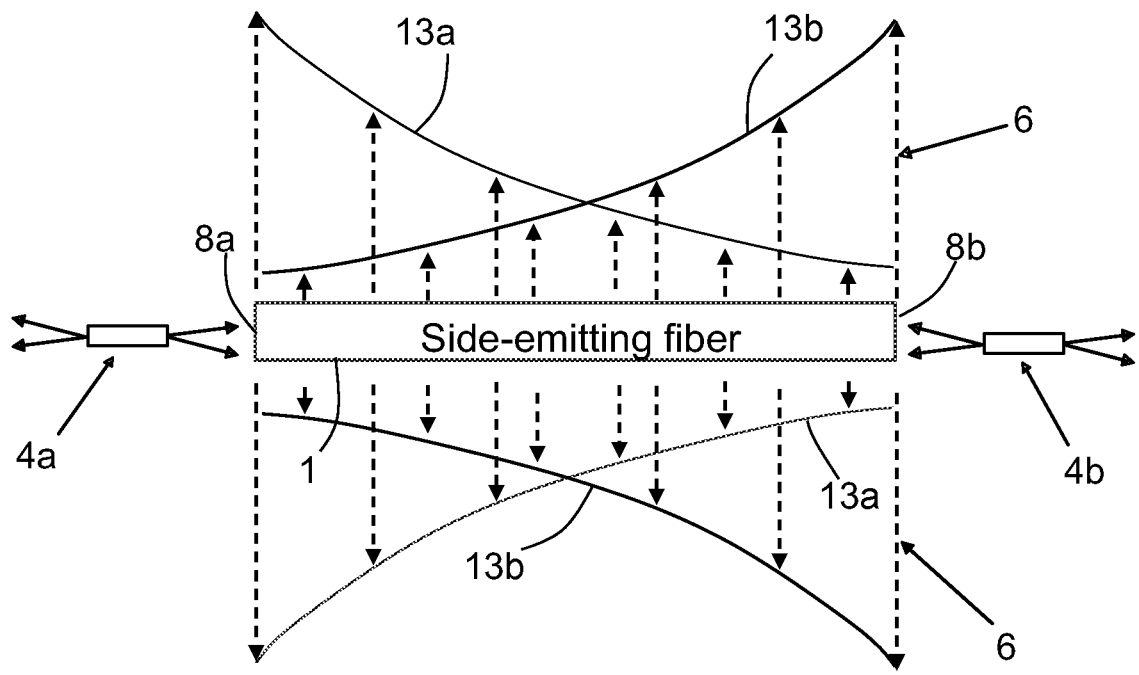
FIG. 2 is a diagram showing respective UV-C light intensity profiles along a side-emitting optical fiber with both end faces optically coupled to respective edge-emitting UV-C laser diodes.

FIG. 2 is a diagram showing respective UV-C light intensity profiles 13a and 13b along a side-emitting optical fiber 2 with both end faces 8a and 8b optically coupled to respective edge-emitting UV-C laser diodes 4a and 4b. With this arrangement, the decrease in intensity of laser light entering at one end face 8a of the side-emitting optical fiber 2 is compensated by the laser light entering at the other end face 8b of the side-emitting optical fiber 2. With proper selection of the output power of the two edge-emitting UV-C laser diodes 4a and 4b and the loss factor (attenuation vs. distance) of the side-emitting optical fiber 2, substantially uniform UV-C intensity of the laser light emitted from the side of the optical fiber can be achieved.

Figure 3:
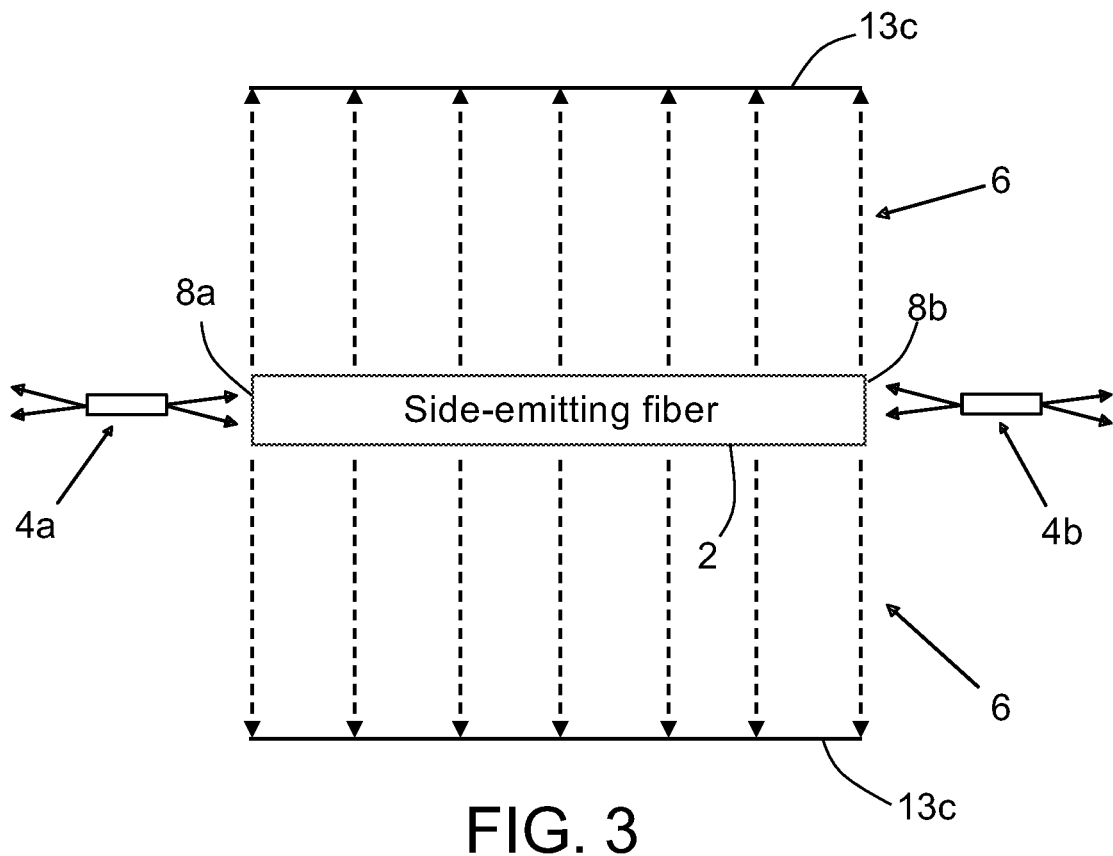
FIG. 3 is a diagram showing uniform light emission from a side-emitting optical fiber with both end faces optically coupled to respective edge-emitting UV-C laser diodes.

FIG. 3 is a diagram showing uniform light emission from a side-emitting optical fiber 2 with both end faces optically coupled to respective edge-emitting UV-C laser diodes 4a and 4b. The light intensity profile 13c is formed by summing the light intensity profiles 13a and 13b shown in FIG. 3.

Figure 4:
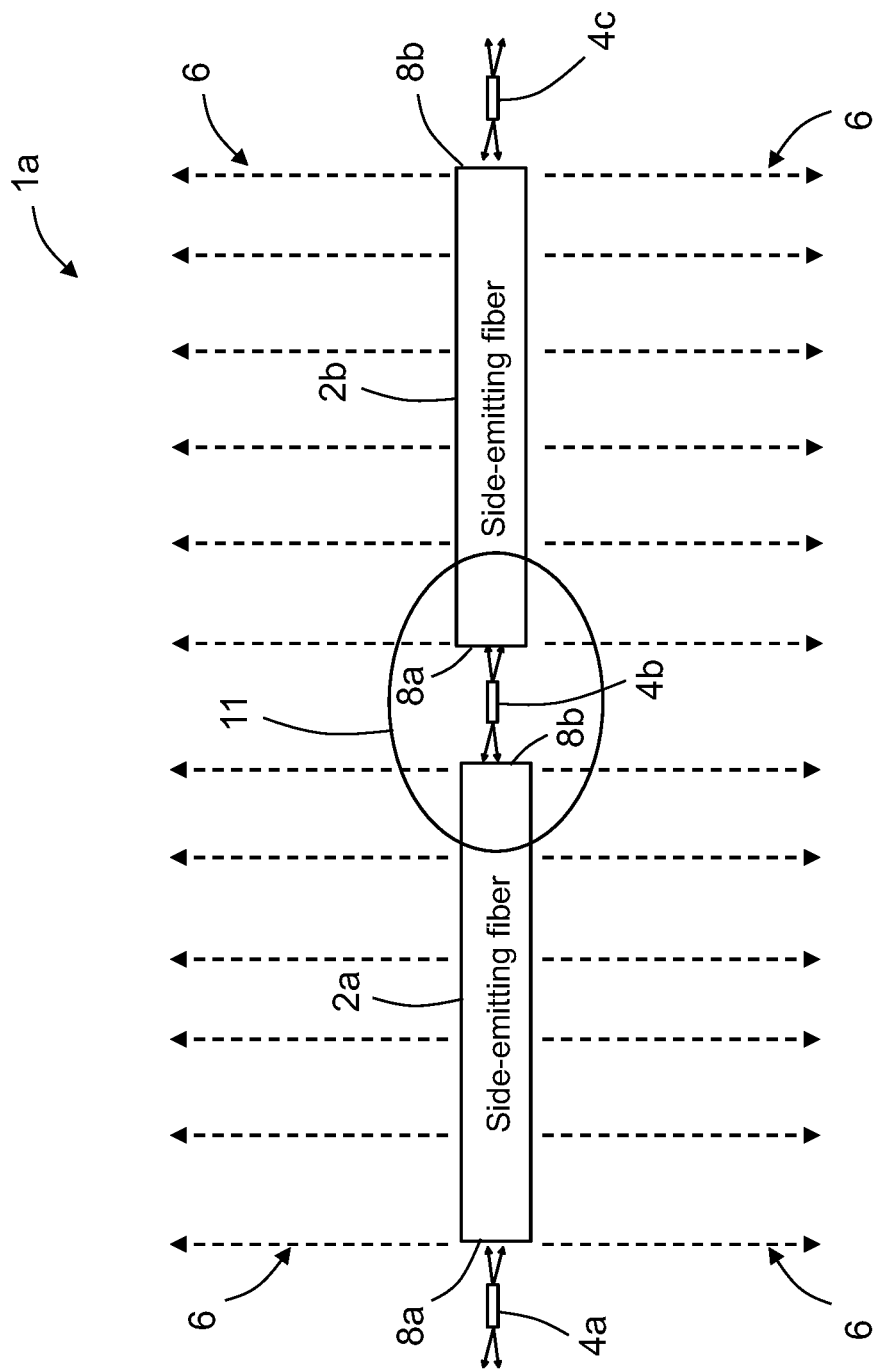
FIG. 4 is a diagram showing uniform light emission from two side-emitting optical fibers interleaved to receive UV-C laser light from three UV-C laser diodes.

FIG. 4 is a diagram showing uniform light emission from two side-emitting optical fibers interleaved to receive UV-C laser light from three UV-C laser diodes. More specifically, the components of the optical disinfection system 1a depicted in FIG. 4 include a first side-emitting optical fiber 2a that receives UV-C laser light at opposing end faces 8a and 8b from a first UV-C laser diode 4a (hereinafter "UV-C laser diode 4a") and a second UV-C laser diode 4b (hereinafter "UV-C laser diode 4b") respectively, whereas a second side-emitting optical fiber 2b receives UV-C laser light at opposing end faces 8a and 8b from UV-C laser diode 4b and a third UV-C laser diode 4c (hereinafter "UV-C laser diode 4c") respectively. In accordance with one embodiment, the side-emitting optical fibers 2a and 2b are of a type having a scattering region surrounding the core (but inside the cladding) in which scattering particles are embedded in glass, and the UV-C laser diodes 4a-4c are of the edge-emitting type.

In accordance with one embodiment, each UV-C laser diode is an edge-emitting semiconductor chip with cleaved facets. The solid arrows emanating from the laser diodes depicted in FIG. 4 represent UV-C laser light 6 emitted from opposing edges of the semiconductor chip, which UV-C laser light enters the adjacent side-emitting optical fiber. For example, some UV-C laser light emitted by UV-C laser diode 4a enters one end face 8a of side-emitting optical fiber 2a and some UV-C laser light emitted by UV-C laser diode 4b enters the other end face 8b of side-emitting optical fiber 2a, while other UV-C laser light emitted by UV-C laser diode 4b enters one end face 8a of side-emitting optical fiber 2b and other UV-C laser light emitted by UV-C laser diode 4c enters the other end face 8b of side-emitting optical fiber 2a. As the UV-C laser light propagates inside side-emitting optical fibers 2a and 2b, some of the UV-C laser light 6 is emitted out the sides of the fibers (represented by dashed arrows in FIG. 4). The optical fibers may be placed in strategic positions onboard an aircraft for the purpose of disinfecting space and surfaces in the path of the side-emitted UV-C laser light 6.

The interface 11 of UV-C laser diode 4b and side-emitting optical fibers 2a and 2b is outlined by an ellipse in FIG. 4. The positional relationships of the interfaced components is maintained by an optical subassembly (OSA) housing (not shown in FIG. 4, but described later with reference to FIGS. 9A and 9B). More specifically, the UV-C laser diode 4b and side-emitting optical fibers 2a and 2b are seated in respective channels of the OSA housing so that respective maximum amounts of UV-C laser light emitted from opposing edges of UV-C laser diode 4b respectively enter side-emitting optical fibers 2a and 2b.

FIG. 5 is a diagram showing uniform light emission from four side-emitting optical fibers 2a-2d interleaved to receive UV-C laser light from five UV-C laser diodes 4a-4e. More specifically, the components of the optical disinfection system 1b depicted in FIG. 5 include the following: a first side-emitting optical fiber 2a that receives UV-C laser light at opposing end faces 8a and 8b from a first UV-C laser diode 4a (hereinafter "UV-C laser diode 4a") and a second UV-C laser diode 4b (hereinafter "UV-C laser diode 4b") respectively; a second side-emitting optical fiber 2b that receives UV-C laser light at opposing end faces 8a and 8b from UV-C laser diode 4b and a third UV-C laser diode 4c (hereinafter "UV-C laser diode 4c") respectively; a third side-emitting optical fiber 2c that receives UV-C laser light at opposing end faces 8a and 8b from UV-C laser diode 4c and a fourth UV-C laser diode 4d (hereinafter "UV-C laser diode 4d") respectively; and a fourth side-emitting optical fiber 2d that receives UV-C laser light at opposing end faces 8a and 8b from UV-C laser diode 4d and a fifth UV-C laser diode 4e respectively;

FIG. 6 is a diagram showing an optical disinfection system 1c which is configured to illuminate a large and long rectangular area for virus disinfection in accordance with one proposed implementation. In this example, the optical disinfection system 1c is a closed-loop arrangement of ten side-emitting optical fibers 2a-2j interleaved with ten edge-emitting UV-C laser diodes 4a-4j. However, any number of side-emitting optical fibers may be interleaved with the same number edge-emitting UV-C laser diodes to form a closed loop. In alternative embodiments, parallel strings of interleaved optical fibers and laser diodes may be substituted for a closed-loop arrangement. For example, the curved side-emitting optical fibers 2e and 2j shown in FIG. 6 may be excluded, leaving one string consisting of four side-emitting optical fibers 2a-2d interleaved with five edge-emitting UV-C laser diodes 4a-4e and another string consisting of four side-emitting optical fibers 2f-2i interleaved with five edge-emitting UV-C laser diodes 4f-4j.

Figure 7:
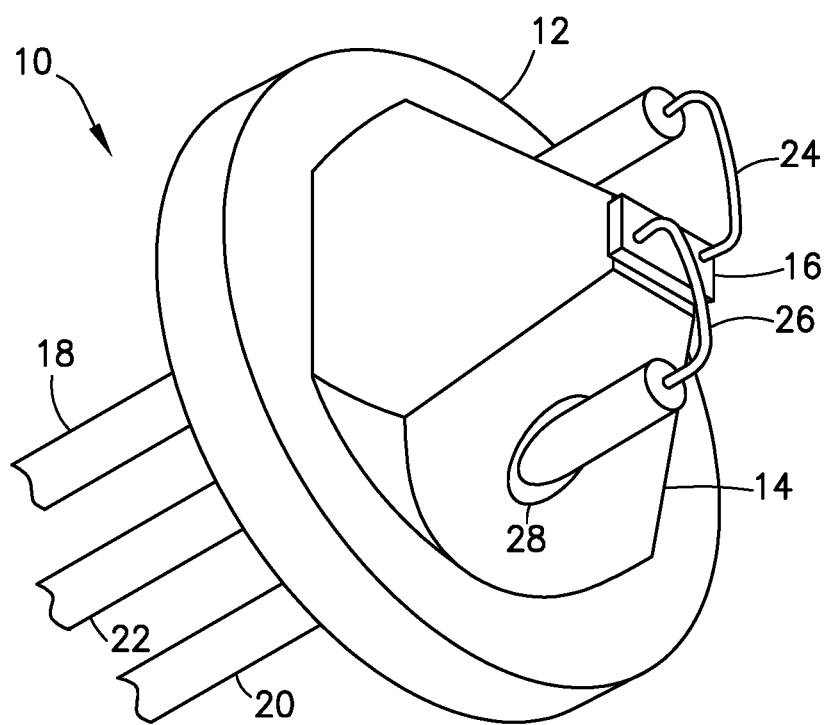
FIG. 7 is a diagram representing a three-dimensional view of a laser package that includes a UV-C laser diode mounted on top of a heat sink in accordance with one proposed implementation.

FIG. 7 is a diagram representing a three-dimensional view of a laser package 10 that includes a UV-C laser diode chip 16 mounted on top of a heat sink 14 in accordance with one proposed implementation. The laser package 10 further includes a Transistor Outline (TO) header having a header base 12. For example, the TO header may have the industrial standard designation "TO 18". The header base 12 has first and second throughholes. The laser package 10 further includes a ground pin 22 having one end connected to the bottom of the header base 12.

Still referring to FIG. 7, the heat sink 14 has a top, a base, and first and second throughholes that pass through the base and not the top. The base of the heat sink 14 is attached to the header base 12 such that the first and second throughholes of heat sink 14 respectively align with the first and second throughholes of header base 12. The laser package 10 further includes: (a) an anode pin 20 that passes through the first throughholes in the header base 12 and heat sink 14 with electrical insulation 28 between the anode pin 20 and the header base 12 and heat sink 14; and (b) a cathode pin 18 that passes through the second throughholes in the header base 12 and heat sink 14 with electrical insulation between the cathode pin 18 and the header base 12 and heat sink 14.

The electrical insulation 28 which surrounds the embedded portions of the anode and cathode pins may be made of solder glass material.

As seen in FIG. 7, the UV-C laser diode chip 16 is attached to the top of the heat sink 14. The top of the heat sink 14 has a first surface area and the base of the heat sink has a second surface area greater than the first surface area. In accordance with one proposed implementation, the heat sink 14 is pyramid-shaped with a truncated top and truncated corners at the base of the heat sink 14.

A first wire 26 connects the UV-C laser diode chip 16 to the anode pin 20. A second wire 24 connects the UV-C laser diode chip 16 to the cathode pin 18. In accordance with at least some embodiments, the UV-C laser diode chip 16 is an edge-emitting laser diode configured to emit UV-C laser light. In accordance with one proposed implementation, the edge-emitting laser diode comprises a quantum well and first and second waveguides disposed on opposite sides of the quantum well active layer (as well be described in more detail below with reference to FIG. 17).

The first step to fabricate the UV-C optical subassembly proposed herein is mounting the heat sink 14 on the header base 12. Then the UV-C laser diode chip 16 is attached on the top of the heat sink 14. The die of the UV-C laser diode chip 16 is bonded to the flat top of the heat sink 14 by eutectic gold-tin (AuSn) solder. Because gold-tin solder has a melting temperature greater than 300° C., the eutectic die bonding process assures that the laser diode is capable of operating at high temperatures with high reliability. Using a heat sink in the form of a pyramid which has a wide area on the bottom enhances the thermal conductivity of the heat sink 14 and lowers the laser diode's junction temperature during continuous operation. After the laser diode chip die bonding has been completed, the top side of the UV-C laser diode chip 16 is wire bonded to the cathode pin 18 and anode pin 20 of the TO header. More specifically, the p-contact pad on UV-C laser diode chip 16 is wire bonded to the anode pin 20; the n-contact pad on of UV-C laser diode chip 16 is wire bonded to the cathode pin 18.

FIG. 8 is a diagram representing a three-dimensional view of some components of an optical subassembly in accordance with one embodiment. The housing of the optical subassembly has been omitted to reveal a laser package 10 (of the type depicted in FIG. 7) situated between respective end faces 8 of side-emitting optical fiber 2 and beneath a transparent window 30. The end sections of side-emitting optical fiber 2 are seated in respective termini 32a and 32b. The end sections (not shown in FIG. 6, but see end sections 34 in FIG. 9A) may be sections at opposite ends of a single optical fiber in the shape of a loop or may be end sections of two different optical fibers (e.g., two coaxial optical fibers separated by a gap, the UV-C laser diode chip 16 being situated in the gap).

The dashed arrows in FIG. 8 represent UV-C laser light emitted by the UV-C laser diode chip 16. Some edge-emitted UV-C laser light 9a enters the side-emitting optical fiber seated in the terminus 32a at end face 8; other edge-emitted UV-C laser light 9b enters the side-emitting optical fiber seated in the terminus 32b at an end face which is not visible in FIG. 6; and some residual UV-C laser light 9c impinges on the transparent window 30 and is transmitted therethrough. The laser package 10, transparent window 30, and termini 32a and 32b are maintained in the respective positions depicted in FIG. 8 by an OSA housing (not shown in FIG. 8).

FIG. 8 shows placement of the UV-C laser package 10 so that the UV-C laser diode chip is aligned with two end faces 8 of side-emitting optical fiber 2 embedded inside respective termini 32a and 32b, with a transparent window 30 overlying the laser diode chip. More specifically, the respective axes of the two end sections of side-emitting optical fiber 2 are aligned with respective edges on opposite sides of the UV-C laser diode chip. The transparent window 30 allows visual observation of the UV-C laser diode chip position and also allows residual UV-C light emission (UV-C laser light 6c in FIG. 8) from the top of the laser diode chip to radiate outward for the purpose of disinfection.

To integrate the components depicted in FIG. 8, the OSA housing 36 is designed to maintain proper alignment of the UV-C laser diode chip 16 with two end faces 8 of side-emitting optical fiber 2 and with transparent window 30 which overlies the UV-C laser diode chip 16. In accordance with one proposed implementation, the OSA housing 36 is an aluminum module with openings at each end which respectively receive the termini 32a and 32b. In addition, the OSA housing 36 has an opening on one face that receives the transparent window 30 and an opening on the opposite face through which the laser package 10 (see FIG. 7) is inserted into the OSA housing 36.

FIG. 9A show the inside view of the OSA housing 36 with all the components assembled together. The termini 32a and 32b are retained in first and second channels 90 and 92 of the OSA housing 36 by termini retainer clips 42a and 42b. The laser package 10 is inserted into the OSA housing 36 via a third channel 94. The header base 12 of laser package is affixed to the top opening of the third channel 94. The transparent window 30 is affixed to a recessed top opening of the fourth channel 94. In accordance with one proposed implementation, both top openings are circular, as are the header base 12 and transparent window 30.

As best seen in FIG. 9B, the first and second channels 90 and 92 are mutually coaxial. Likewise, the third and fourth channels 94 and 96 are mutually coaxial. In accordance with one proposed implementation, the axis of the first and second channels 90 and 92 is perpendicular to the axis of the third and fourth channels 94 and 96. All of the four channels intersect at a central space 88 in the middle of the OSA housing 36. More specifically, each of the first and second channels 90 and 92 consists of two circular cylindrical sections having different diameters slightly greater than the outer diameters of respective sections of the termini 32a and 32b. The third channel 94 is circular cylindrical. The fourth channel 96 includes a recessed circular top opening 40 having an offset that forms a seat 98 for the transparent window 30. The fourth channel 96 also includes a conical section that connects the central space 88 to the recessed top opening. The diameter of the conical section of the fourth channel 96 increases in the direction from the central space 88 to the transparent window 30 (see FIG. 9A).

In accordance with the configuration depicted in FIG. 9A, the UV-C laser diode chip 16 is situated precisely at the center of the central space 88. More specifically, the header base 12 of the laser package 10 is attached to the top opening of the third channel 94 of the OSA housing 36 by high-temperature, non-conductive, space-grade epoxy. The transparent window 30 is attached to the recessed top opening of the fourth channel 96 of the OSA housing 36 by space-grade optically transparent epoxy. The transparent window 30 is located above the UV-C laser diode chip 16 to facilitate observation of the laser diode chip position during the process of assembling the optical subassembly 15. The transparent window 30 also allows residual UV-C laser light emitted from the top of the UV-C laser diode chip 16 to exit the OSA housing 36 to provide additional virus-disinfecting UV-C laser light in the space and on surfaces in the path of that propagating light.

When all the components are assembled together as shown in FIG. 9A, the two edges of the UV-C laser diode chip 16 are optimally aligned to the two end sections 34 of side-emitting optical fiber respectively disposed inside the termini 32a and 32b. The transparent window 30 is also at a position which maximizes the UV-C laser light collected from the top of the laser diode chip 16.

Figure 10:
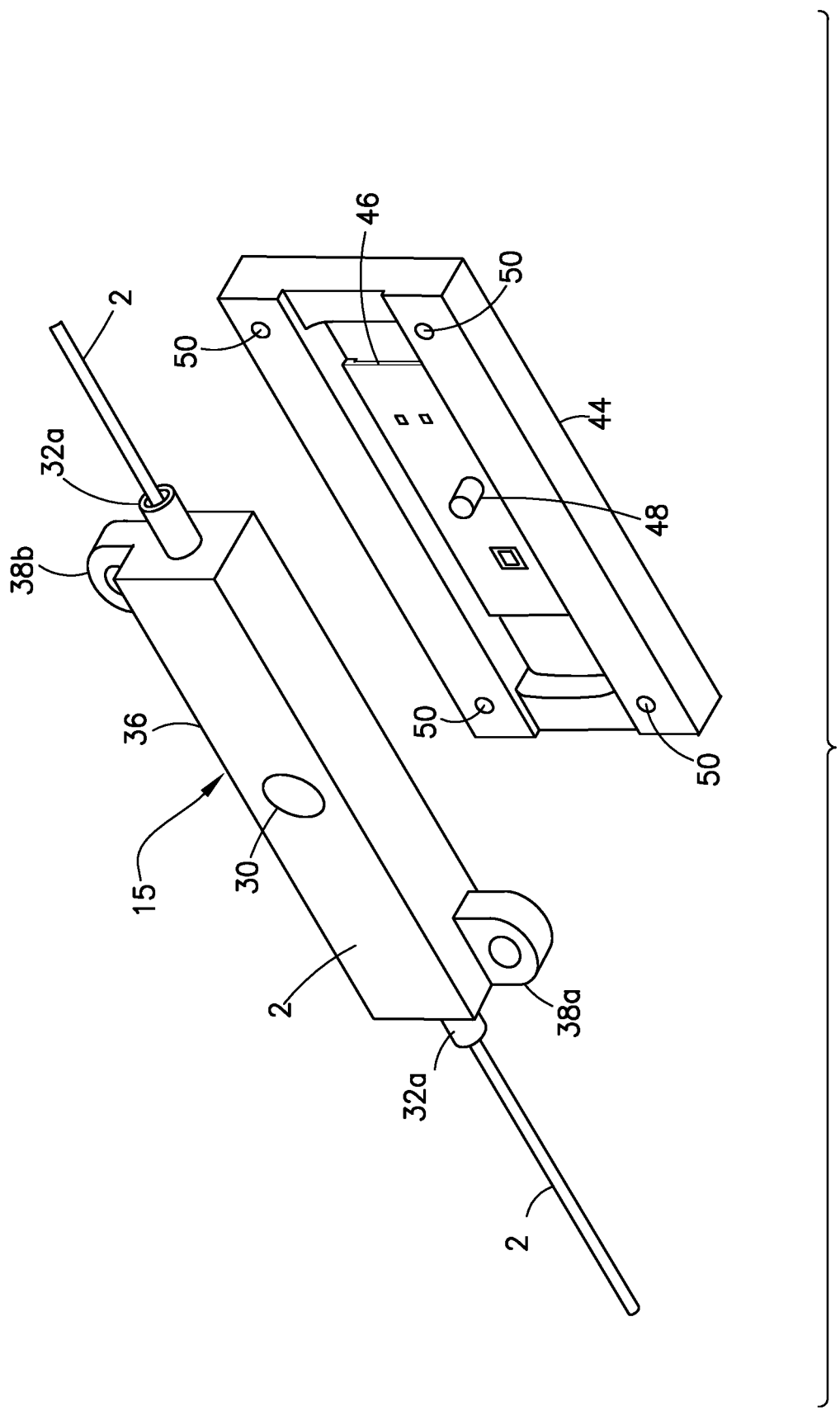
FIG. 10 is a diagram representing a three-dimensional view of the optical subassembly depicted in FIG. 9A and an electronics housing (which has a printed wiring board mounted thereon) prior to their assembly.

FIG. 10 is a diagram representing a three-dimensional view of the optical subassembly 15 and electronics housing 44 prior to their assembly. The OSA housing 36 has two flanges 38a and 38b on two sides for mounting to electronics housing 44. In accordance with one proposed implementation, the electronics housing 44 is an aluminum module which contains a UV-C laser driver electronics printed wiring board 46 (hereinafter "PWB 46"). A three-pin socket 48 is located in the center of PWB 46 to connect the three pins of the UV-C laser package 10 to the electronic components on the PWB 46. The electronics housing 44 also has four mounting holes 50 at the four corners of the housing. Two of the four mounting holes 50 are used to mount the optical subassembly 15 to electronics housing 44; the other two mounting holes 50 are used to mount the completed assembly onto an airplane ceiling or other external fixture, such as a window, a door, a tray, and an overhead storage bin.

Figure 11:
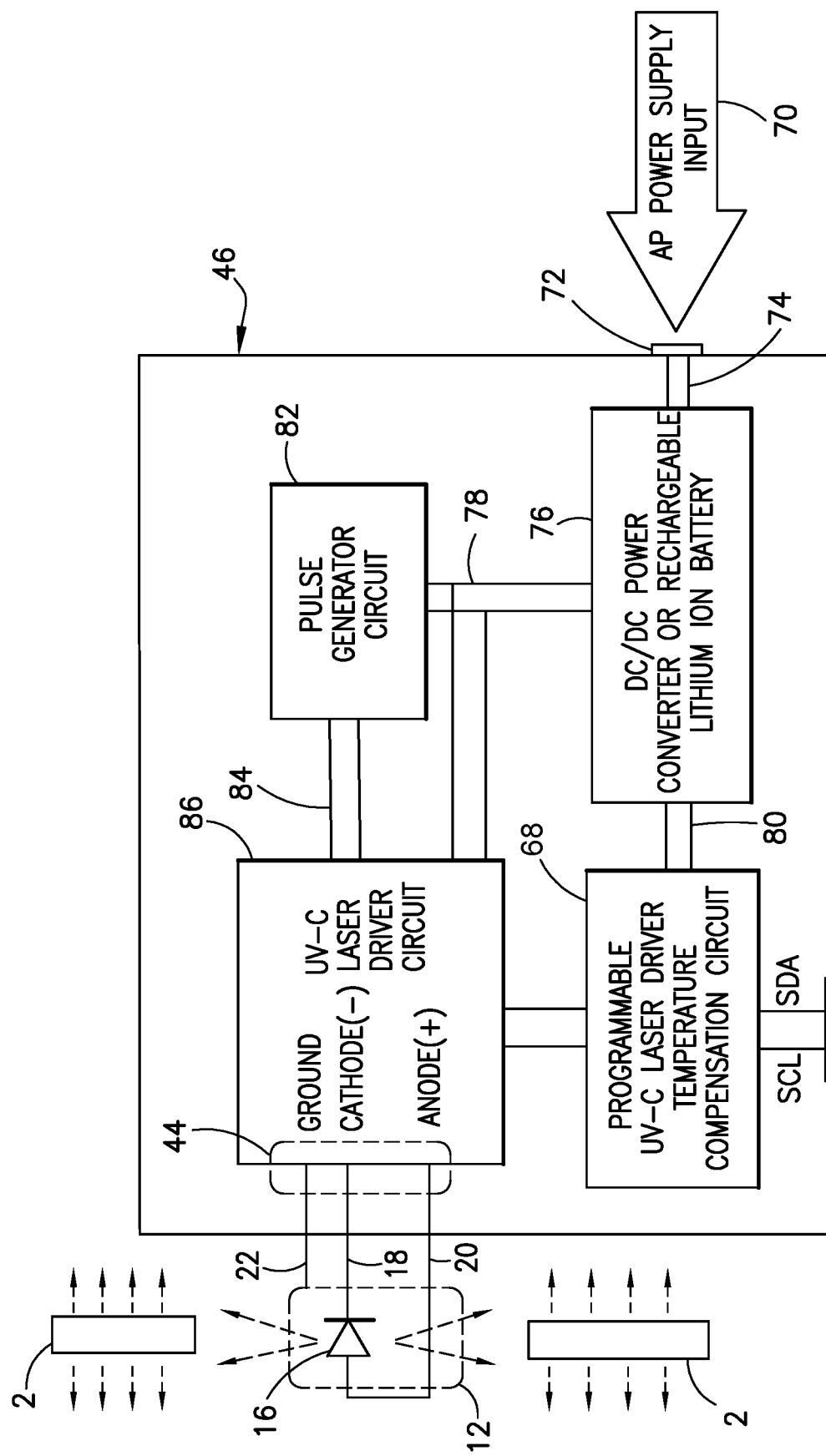
FIG. 11 is a block diagram identifying laser driver electronic circuit components on the printed wiring board which is depicted in FIG. 10.

FIG. 11 is a block diagram identifying laser driver electronic circuit components on the PWB 46 seen in FIG. 10. The UV-C laser diode chip 16 is connected to the PWB 46 through the three-pin socket 48. The laser diode chip's p-contact is connected to the anode pin 20, the laser diode chip's n-contact is connected to the cathode pin 18, and the ground pin 22 is connected to the PWB common ground plane. The pulse generator circuit 82 generates high-speed low-duty-cycle voltage pulses which are input to the UV-C laser driver circuit 86 via high-speed signal line 84. The UV-C laser driver circuit 86 converts the voltage pulses from the pulse generator circuit 82 to current pulses which drive the UV-C laser diode chip 16 to generate high-speed low-duty-cycle UV-C light pulses to perform disinfection.

The UV-C laser driver circuit 86 is also connected to the UV-C laser driver temperature compensation circuit 90, which is configured to stabilize the UV-C laser light output of the UV-C laser diode chip 16 over a temperature range of −40° C. to 100° C. The UV-C laser driver temperature compensation circuit 90 circuit is programmable through a two-pin I²C serial interface. The two pins Serial Data (SDA) and Serial Clock (SCL) are connected to an external computer (not shown in FIG. 11) through a micro-USB connector 88. With this I²C interface, the UV-C laser light output power will remain constant over a wide avionic temperature range using an externally loaded software program in its memory.

The pulse generator circuit 82, UV-C laser driver circuit 86, and UV-C laser driver temperature compensation circuit 90 receive DC power from a DC/DC power converter 76 via DC power supply lines 78 and 80. The DC/DC power converter 76 is connected to receive the airplane's DC power supply input 70 through an avionics qualified power supply connector 72 and via DC power supply line 74. Because standard airplane DC power supply is 28 V, and the circuits inside the PWB 46 need 5 V (or 3.3 V) power supplies, the DC/DC converter's function is to convert the 28-V DC power supply input 70 from the airplane to a 5-V (or 3.3-V) power supply.

Using the PWB design depicted in FIG. 11 to drive UV-C laser pulses at a 10% duty cycle, the UV-C laser's peak optical power will be 10 times higher than the continuous wave optical power. This is a tenfold increase in UV-C optical power to disinfect surfaces in an airplane. The pulse generator circuit 82 provides high-speed voltage pulses with pulse width of 100 nsec or less. Thus, the UV-C laser diode chip 16 outputs high-speed and high-peak-power UV-C laser light which is effective to disinfect a virus because 100 nsec is much faster than the virus replication time. The virus would be killed by the UV-C laser light from the laser before the virus can replicate.

If airplane DC power is not available, a long-operating-time lithium ion battery may be substituted in place of the DC/DC power converter 76 in the PWB design. Using the lithium ion battery, the UV-C optical subassembly can be operated without any external electrical wire connection.

Figure 12:
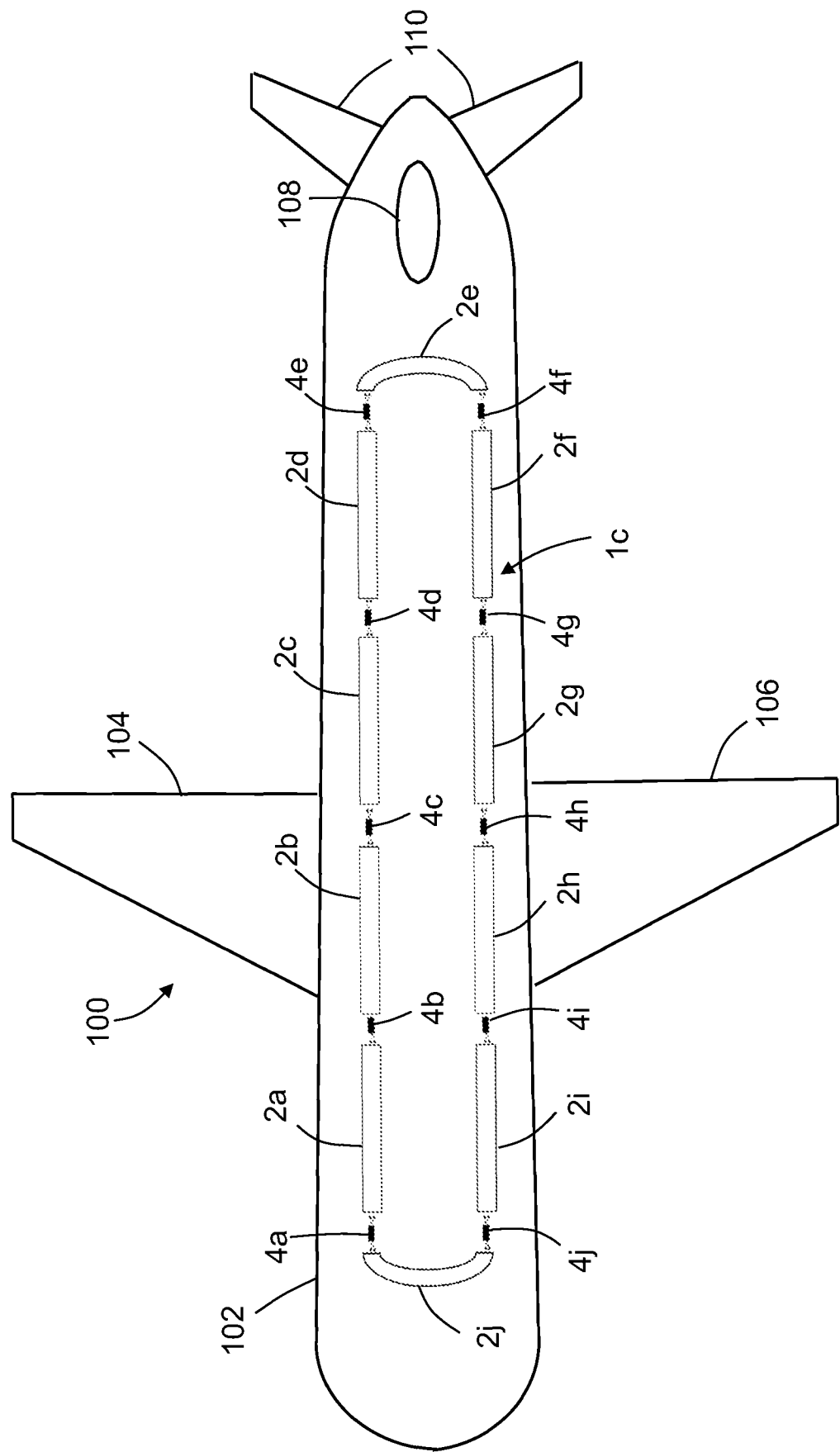
FIG. 12 is a diagram showing the installation of a side-emitting UV-C laser light system of the type depicted in FIG. 6 on the ceiling of an airplane cabin to disinfect the whole cabin area.

FIG. 12 is a diagram showing the installation of an optical disinfection system 1c of the type depicted in FIG. 6 inside the fuselage 102 of a commercial airplane 100 having wings 106 and 106, a vertical stabilizer 108, and a horizontal stabilizer 110. For example, the optical disinfection system 1c may be mounted to the ceiling of the airplane cabin to disinfect the whole cabin area. Depending on the model of the airplane, each straight side-emitting optical fiber 2a-2d and 2f-2i extending parallel to the center axis of the fuselage 102 is in the range of 10 to 20 meters in length, whereas the two slightly curved side-emitting optical fibers 2e and 2j in the forward and aft portions of the fuselage 102 may have a length in the range of 5 to 15 meters. Installing this UV-C side-emitting system in the airplane enables the whole airplane cabin to be safely disinfected without human intervention.

Figure 13:
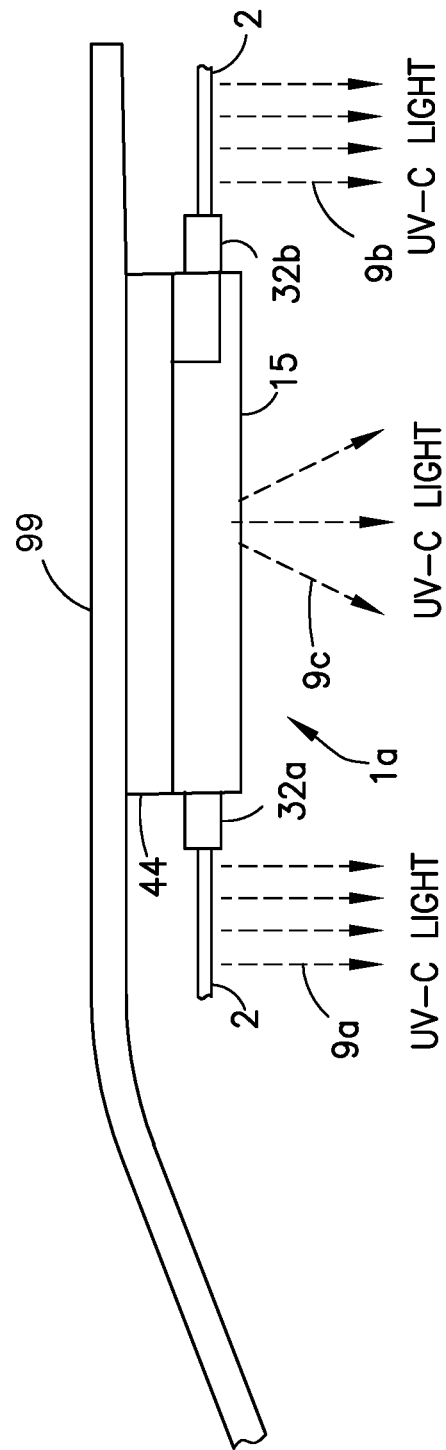
FIG. 13 is a diagram representing a side view of the optical subassembly and electronics housing depicted in FIG. 10 following assembly and installation on the cabin ceiling of an airplane.

FIG. 13 is a diagram representing a side view of the UV-C optical subassembly 15 and electronics housing 44 depicted in FIG. 10 following assembly and installation on the cabin ceiling 99 of an airplane. The UV-C optical subassembly 15 with electronics housing 44 are installed upside down on the cabin ceiling 99. The UV-C laser light 9a and 9b is emitted from side-emitting optical fiber 2 (a single fiber in the shape of a loop or two separate fibers). Also residual UV-C laser light 9c is emitted from the transparent window 30 (not visible in FIG. 16) in the middle of the UV-C optical subassembly 15.

Figure 14B:
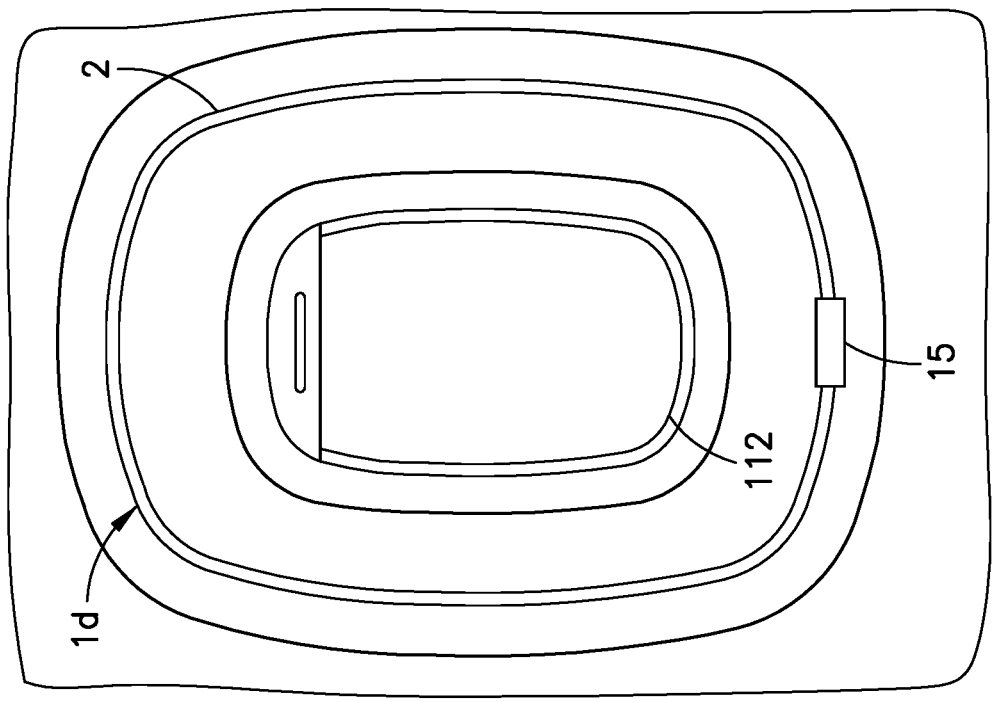
FIG. 14B is a diagram showing installation of the optical disinfection system depicted in FIG. 14A around an airplane window.
Figure 14A:
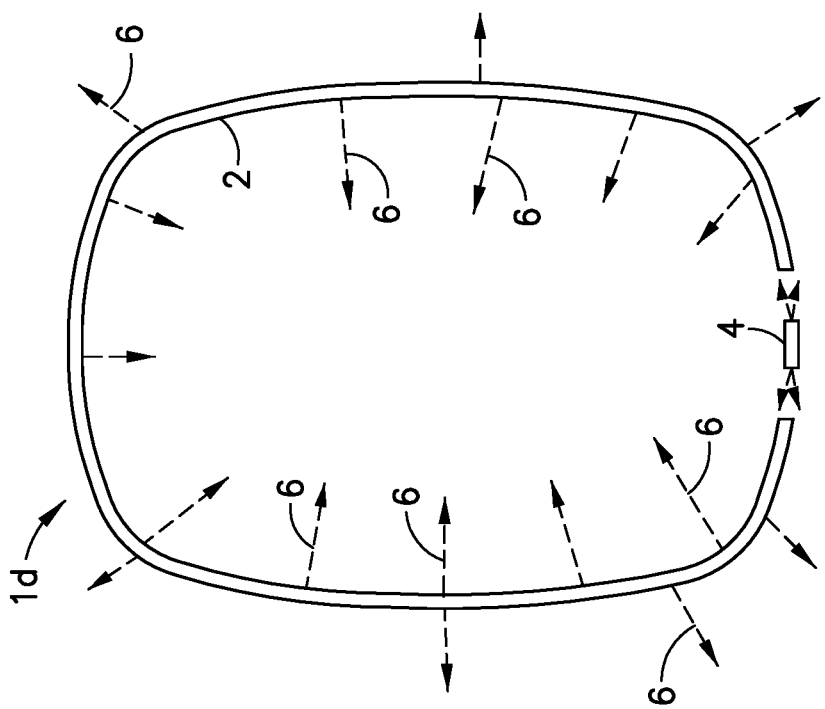
FIGS. 14A, 15A, and 16A are diagrams representing differently shaped loops of a single side-emitting optical fiber having end faces optically coupled to a single UV-C edge-emitting laser diode.
Figure 15A:
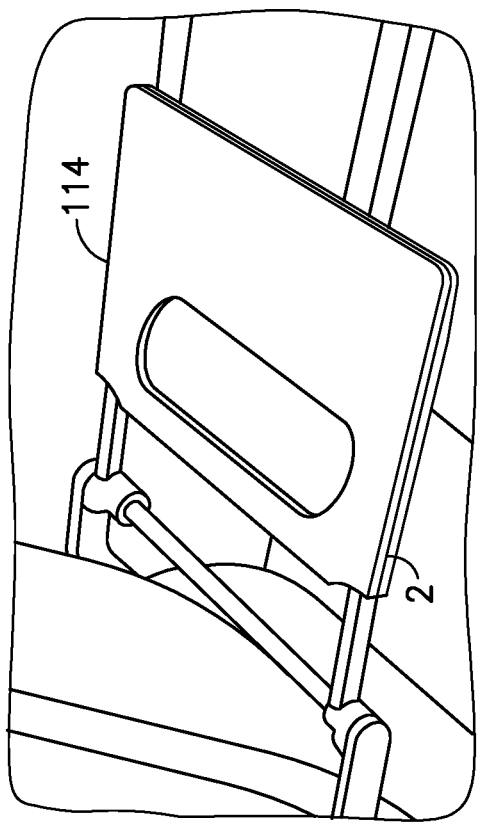
Figure 16B:
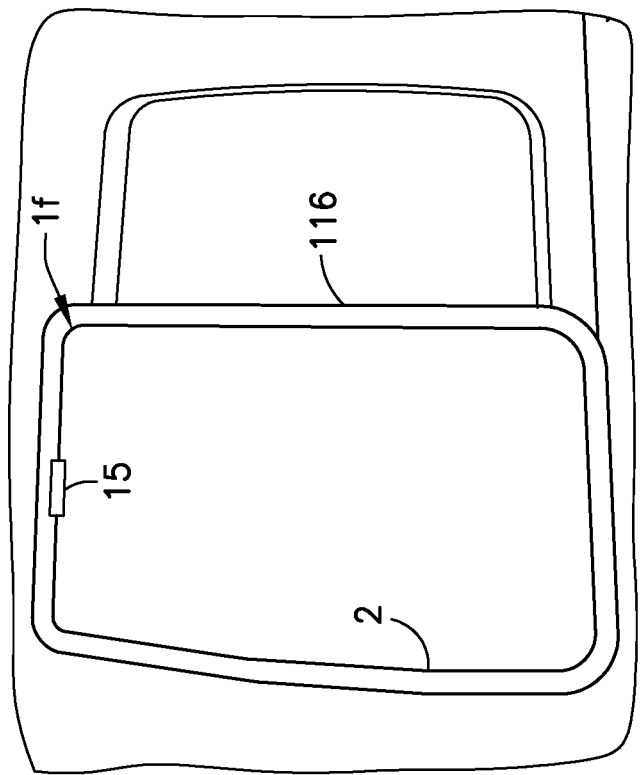
FIG. 16B is a diagram showing installation of the optical disinfection system depicted in FIG. 16A around an airplane door.
Figure 16A:
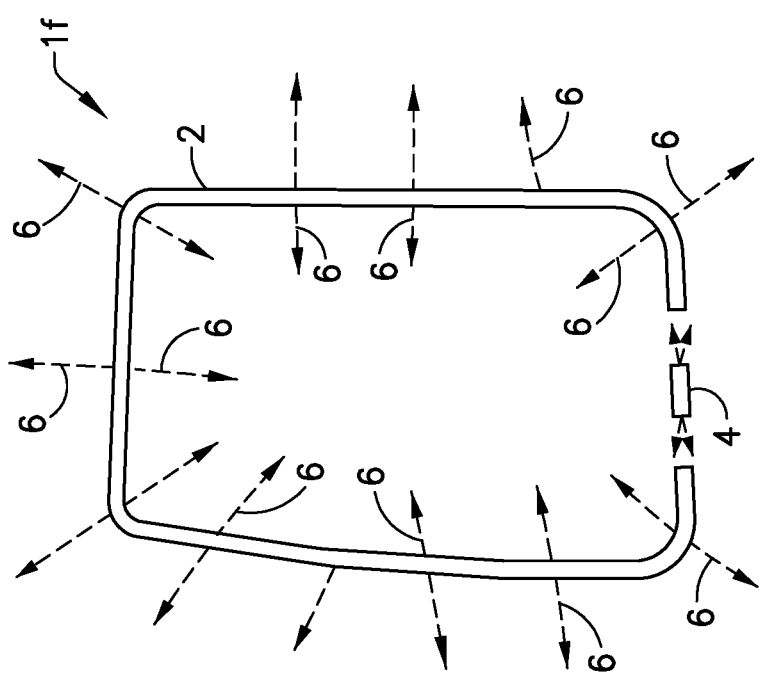

FIGS. 14A, 15A, and 16A are diagrams representing respective optical disinfection systems 1d-1f comprising differently shaped loops of a single side-emitting optical fiber 2 having end faces optically coupled to a single UV-C edge-emitting laser diode 4. (Other components of the optical subassembly 15 are not shown in FIGS. 14A, 15A, and 16A.) There are many areas of a commercial airplane where similar UV-C side-emitting optical fiber systems can be installed, such as flight decks, lavatories, flight attendant stations, passenger cabins, cargo compartments, and electronics bays.

FIG. 14B is a diagram showing installation of the optical disinfection system 1d depicted in FIG. 14A around an airplane window 112. The side-emitting optical fiber 2 may be adhered to the window frame using optically transparent epoxy while the optical subassembly 15 (which includes the UV-C edge-emitting laser diode 4 seen in FIG. 14A) is fastened to the window frame. This arrangement will enhance the disinfection efficiency of the passenger seats adjacent to the windows.

Figure 15B:
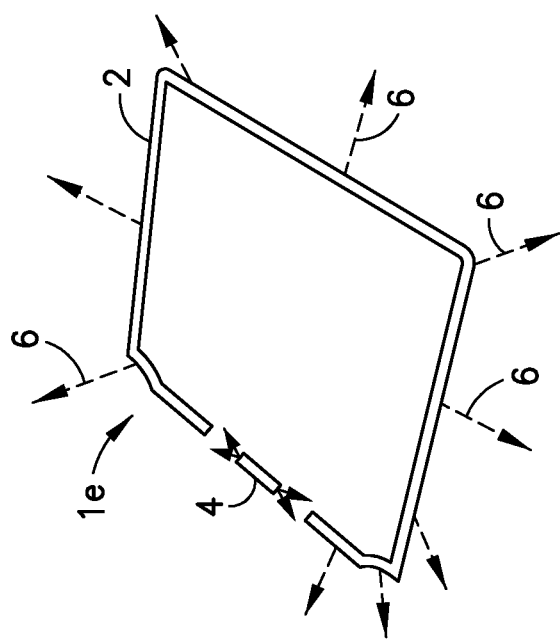
FIG. 15B is a diagram showing installation of the optical disinfection system depicted in FIG. 15A around an airplane passenger tray table.

FIG. 15B is a diagram showing installation of the optical disinfection system 1e depicted in FIG. 15A around the perimeter of an airplane passenger tray table 114. In this instance, the side-emitting optical fiber 2 is adhered to the edge of airplane passenger tray table 114 using optically transparent epoxy. The airplane passenger tray table 114 can be arranged to be continuously disinfected when the tray table is latched to the back of the passenger seat.

FIG. 16B is a diagram showing installation of the optical disinfection system 1f depicted in FIG. 16A around an airplane door 116. In this instance, the side-emitting optical fiber 2 is adhered to the interior surface of airplane door 116 using optically transparent epoxy, while the optical subassembly 15 (which includes the UV-C edge-emitting laser diode 4 seen in FIG. 16A) is fastened to the interior surface of airplane door 116. This arrangement will enhance the disinfection efficiency around the area near the airplane's doors (typically the area near the door is the flight attendants' station).

Figure 17:
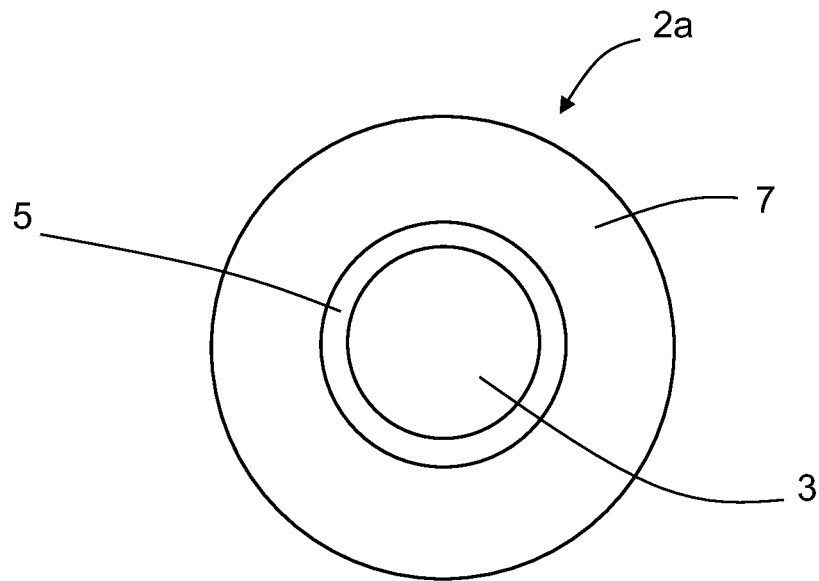
FIG. 17 is a diagram representing an end view of one type of side-emitting optical fiber.

FIG. 17 is a diagram representing an end view of one type of side-emitting step-index optical fiber 2a which is suitable for use in the optical disinfection system disclosed herein. A step-index optical fiber has a refractive index profile characterized by a uniform refractive index within the core and a sharp decrease in refractive index at the core-cladding interface so that the cladding has a lower refractive index. The side-emitting step-index optical fiber 2a shown in FIG. 17 has a scattering region 5 made from a glass with embedded scattering particles (not shown in FIG. 17) and located between the core 3 and cladding 7. The scattering region 5 surrounds the core 3. Some of the light propagating through the core 3 is scattered radially outward through the cladding 7 due to the presence of the scattering particles.

Figure 18:
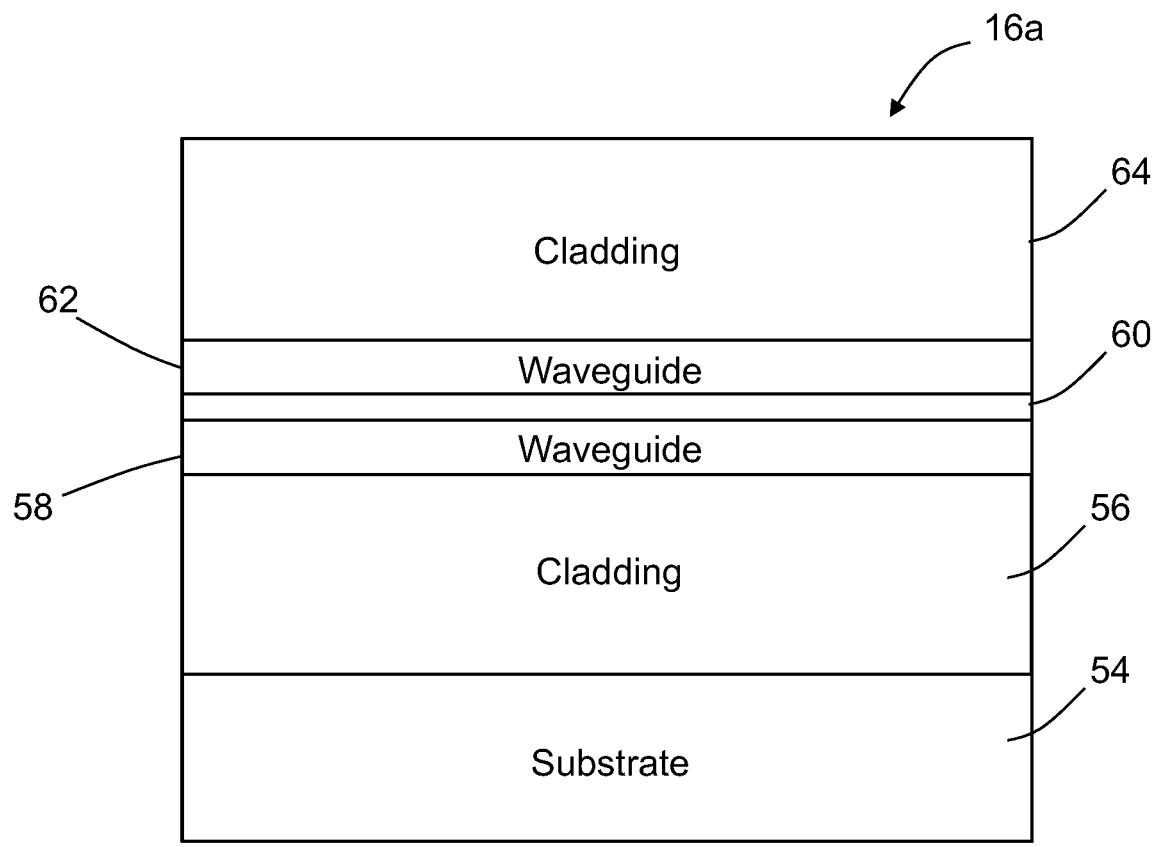
FIG. 18 is a diagram representing an end view showing some layers in a UV-C edge-emitting laser diode semiconductor chip.

FIG. 18 is a diagram representing an end view showing some layers in a UV-C edge-emitting laser diode semiconductor chip 16a. Semiconductor lasers are typically fabricated on a wafer by growing layered semiconductor material on a substrate 54 to form an epitaxial structure having an active layer 60 parallel to the substrate surface. The wafer is then processed with a variety of semiconductor processing tools to produce a laser optical cavity incorporating the active layer 60 and metallic contacts (not shown in FIG. 18) attached to the semiconductor material. Laser mirror edges typically are formed at the ends of the laser cavity by cleaving or etching. Within the edge-emitting laser structure, the laser light is guided in a p-side waveguide 62 and an n-side waveguide 58 which sandwich the active layer 60. The layers in UV-C edge-emitting laser diode semiconductor chip 16a further include n-side cladding 56 grown on substrate 54 and p-side cladding 64 grown on p-side waveguide 62.

In 2019, a description of a laser structure that generates UV-C light effectively, emitting at 271.8 nm, was published by Nagoya University and Asahi Kasei Corporation. The key technical accomplishment of this UV-C laser development is a high-quality single-crystal aluminum nitride (AlN) substrate 54 and the aluminum composition gradient in the cladding (optical confinement) layers, which minimize defects in the active layer 60 of the laser diode. More specifically, the reported laser structure had an n-side cladding 56 made from $Al_{0.7}Ga_{0.3}N$, an n-side waveguide 58 made from $Al_{0.63}Ga_{0.37}N$, an active layer 60 in the form of a single quantum well, a p-side waveguide 62 made from $Al_{0.63}Ga_{0.37}N$, and a p-side cladding 64 which is distributed polarization doped. More details of this laser structure are provided by Zhang et al. in: "A 271.8 nm deep-ultraviolet laser diode for room temperature operation," Applied Physics Express 12, 124003 (2019), published by The Japan Society of Applied Physics.

In summary, the optical subassembly design proposed herein may be used in an UV-C virus optical disinfection system inside an airplane. The proposed optical subassembly has a high peak output power and high reliability. This optical subassembly can be operated with either a standard airplane 28-V power supply or a battery in case an external power supply is not available or feasible.

While optical disinfection systems having side-emitting optical fiber optically coupled to a UV-C laser diode have been described with reference to various embodiments, it will be understood by those skilled in the art that various changes may be made and equivalents may be substituted for elements thereof without departing from the teachings herein. In addition, many modifications may be made to adapt the concepts and reductions to practice disclosed herein to a particular situation. Accordingly, it is intended that the subject matter covered by the claims not be limited to the disclosed embodiments.

The invention claimed is:

1. A UV-C lighting system comprising: a plurality of housings, wherein each housing comprises a central space and first through fourth channels which intersect the central space; a plurality of side-emitting optical fibers, wherein each side-emitting optical fiber comprises a first end section terminating at a first end face configured to receive UV-C light, a second end section terminating at a second end face configured to receive UV-C light, and a side configured to side emit UV-C light received by either of the first and second end faces; a plurality of UV-C laser light sources, wherein each UV-C laser light source is configured to emit UV-C laser light and housed in a respective housing; a plurality of windows, wherein each window is optically transparent and supported by a respective housing, wherein the first and second channels of each housing are co-axial with each other along a first axis, configured to receive UV-C light and the third and fourth channels of each housing are co-axial with each other along a second axis which is disposed perpendicular to the first axis; wherein the first end section of one side-emitting optical fiber of the plurality of side-emitting optical fibers is disposed in the first channel of one housing of the plurality of housings, the second end section of a not her side-emitting optical fiber of the plurality of side-emitting optical fibers is disposed in the second channel of the one housing, one UV-laser light source of the plurality of UV-C laser light sources is disposed in the central space of the one housing, and one window of the plurality of windows is disposed in the fourth channel of the one housing, wherein the one UV-C laser light source is configured to emit first UV-C laser light that impinges on the first end face of the one side-emitting optical fiber and second UV-C laser light that impinges on the second end face of the another side-emitting optical fiber, and wherein the one window is configured to transmit impinging third UV-C laser light emitted by the one UV-C laser light source.

2. The UV-C lighting system as recited in claim 1, wherein the one UV-C laser light source comprises a laser package that is seated in a top opening of the third channel of the one housing.

3. The UV-C lighting system as recited in claim 1, further comprising:
a first terminus surrounding the first end section of the one side-emitting optical fiber; and
a second terminus surrounding the second end section of the another optical fiber,
wherein the first terminus is seated in the first channel of the one housing and the second terminus is seated in the second channel of the one housing.

4. The UV-C lighting system as recited in claim 1, wherein the one UV-C laser light source comprises an edge-emitting laser diode.

5. The UV-C lighting system as recited in claim 1, wherein each one side-emitting optical fiber is a step-index fiber comprising a light-guiding core and a transparent or translucent cladding surrounding the core and separated from the core by a scattering region, wherein the light-guiding core is made of glass having a first refractive index, the cladding is made of glass having a second refractive index less than the first refractive index, and the scattering region comprises a glass matrix with embedded particles.

6. The UV-C lighting system as recited in claim 1, wherein the fourth channel of the one housing has a recessed top opening that forms an offset and the one window is seated on the offset.

7. The UV-C lighting system as recited in claim 6, wherein the fourth channel includes a conical section that connects the central space of the one housing to the recessed top opening.

8. A UV-C lighting system comprising:
a laser package comprising a UV-C laser light source configured to emit first UV-C laser light in one direction and second UV-C laser light in an opposite direction;
a side-emitting optical fiber having a first end section that terminates at a first end face which is disposed to receive UV-C laser light emitted in the one direction by the UV-C laser light source and a second end section that terminates at a second end face which is disposed to receive UV-C laser light emitted in the opposite direction by the UV-C laser light source;
a first terminus surrounding the first end section of the side-emitting optical fiber;
a second terminus surrounding the second end section of the side-emitting optical fiber;
a window; and
a housing having a first channel in which the first terminus is seated, a second channel in which the second terminus is seated, a third channel in which the laser package is seated, a fourth channel in which the window is seated, and a central space which is intersected by the first through fourth channels,
wherein the first and second channels are mutually coaxial along a first axis, the third and fourth channels are mutually coaxial along a second axis, the first axis is perpendicular to the second axis, and the UV-C laser light source is disposed in the central space.

9. The UV-C lighting system as recited in claim 8, wherein the UV-C laser light source comprises an edge-emitting laser diode.

10. The UV-C lighting system as recited in claim 8, wherein each side-emitting optical fiber is a step-index fiber comprising a light-guiding core and a transparent or translucent cladding surrounding the core and separated from the core by a scattering region, wherein the light-guiding core is made of glass having a first refractive index, the cladding is made of glass having a second refractive index less than the first refractive index, and the scattering region comprises a glass matrix with embedded particles.

11. The UV-C lighting system as recited in claim 8, wherein the laser package is seated in a top opening of the third channel.

12. The UV-C lighting system as recited in claim 8, wherein the fourth channel has a recessed top opening that forms an offset and the window is seated on the offset.

13. The UV-C lighting system as recited in claim 12, wherein the fourth channel includes a conical section that connects the central space to the recessed top opening.

14. A UV-C lighting system comprising:
- a laser package comprising a first laser diode configured to emit UV-C laser light;
- first and second side-emitting optical fibers, each side-emitting fiber comprising a first end section terminating at a first end face, a second end section terminating at a second end face configured to receive UV-C light, and a side configured to side emit UV-C light received by either of the first and second end faces;
- a first terminus surrounding the first end section of the first side-emitting optical fiber;
- a second terminus surrounding the second end section of the second side-emitting optical fiber;
- a window; and
- a housing having a first channel in which the first terminus is seated, a second channel in which the second terminus is seated, a third channel in which the laser package is seated, a fourth channel in which the window is seated, and a central space which is intersected by the first through fourth channels,
- wherein the first and second channels are mutually coaxial along a first axis, the third and fourth channels are mutually coaxial along a second axis, the first axis is perpendicular to the second axis, and the first laser diode is disposed in the central space;
- wherein the first laser diode is configured to emit first UV-C laser light in one direction and second UV-C laser light in an opposite direction; and
- wherein the first end face of the first side-emitting optical fiber is disposed to receive UV-C laser light emitted in the one direction by the first laser diode and the second end face of the second side-emitting optical fiber is disposed to receive UV-C laser light emitted in the opposite direction by the first laser diode.

15. The UV-C lighting system as recited in claim 14, further comprising second and third laser diodes configured to emit UV-C laser light, wherein the second end face of the first side-emitting optical fiber is disposed to receive UV-C laser light emitted by the second laser diode and the first end face of the second side-emitting optical fiber is disposed to receive UV-C laser light emitted by the third laser diode.

16. The UV-C lighting system as recited in claim 14, wherein the first laser diode comprises an edge-emitting laser diode.

17. The UV-C lighting system as recited in claim 14, wherein the first side-emitting optical fiber is a step-index fiber comprising a light-guiding core and a transparent or translucent cladding surrounding the core and separated from the core by a scattering region, wherein the light-guiding core is made of glass having a first refractive index, the cladding is made of glass having a second refractive index less than the first refractive index, and the scattering region comprising a glass matrix with embedded particles.

18. The UV-C lighting system as recited in claim 14, wherein the laser package is seated in a top opening of the third channel of the housing.

19. The UV-C lighting system as recited in claim 14, wherein the fourth channel has a recessed top opening that forms an offset and the window is seated on the offset.

20. The UV-C lighting system as recited in claim 19 wherein the fourth channel of the housing includes a conical section that connects the central space to the recessed top opening.

\* \* \* \* \*